United States Patent [19]
Mach et al.

[11] Patent Number: 6,022,682
[45] Date of Patent: Feb. 8, 2000

[54] ARTICLE AND METHOD FOR DETECTION OF ENTEROTOXIGENIC STAPHYLOCOCCI

[75] Inventors: Patrick A. Mach, Shorewood; Marlys E. Lund, Eden Prairie, both of Minn.

[73] Assignee: Minnesota Mining and Manufacturing Company, St. Paul, Minn.

[21] Appl. No.: 08/696,385

[22] Filed: Aug. 14, 1996

[51] Int. Cl.$^7$ .................................................. C12Q 1/04
[52] U.S. Cl. .................. 435/4; 435/18; 435/34; 435/36; 435/40; 435/882; 435/883; 435/805; 435/287.2
[58] Field of Search .................................. 435/4, 18, 34, 435/36, 40, 287.2, 882, 883, 805

[56] References Cited

U.S. PATENT DOCUMENTS

| | | | |
|---|---|---|---|
| 4,241,181 | 12/1980 | Lund | 435/34 |
| 4,565,783 | 1/1986 | Hansen et al. | 435/299 |
| 5,137,812 | 8/1992 | Matner | 435/38 |
| 5,232,838 | 8/1993 | Nelson et al. | 435/30 |
| 5,443,963 | 8/1995 | Lund | 435/34 |
| 5,496,706 | 3/1996 | Kuusela et al. | 435/7.33 |

FOREIGN PATENT DOCUMENTS

| | | |
|---|---|---|
| WO 93/12218 | 6/1993 | WIPO . |
| WO 95/20674 | 8/1995 | WIPO . |

OTHER PUBLICATIONS

V. Ruzickova, "Rapid Method for Detecting Thermostable Nuclease in Staphylococci," *Folia Microbiologica*, vol. 36, No. 6, pp. 582–584 (1991).

Kamman et al., Optimal Conditions For Assay Of Staphylococcal Nuclease, J. of Food Science, vol. 42, No. 2 pp. 421–424 (1977).

Lachica, Accelerated Procedure for the Enumeration and Identification of Food–Borne *Staphylococcus aureus*, Applied and Environment Microbiology, vol. 39, No. 1, pp. 17–19 (1980).

Lachica, Simplified Thermonuclease Test for Rapid Identification of *Staphylococcus aureus* Recovered on Agar Media, Applied and Environment Microbiology, vol. 32, No. 4, pp. 633–634 (1976).

Lachica et al., Metachromatic Agar–Diffusion Methods for Detecting Staphylococcal Nuclease Activity, Applied Microbiology, vol. 21, No. 4, pp. 585–587 (1971).

Waller et al., Improvement to Two Toluidine Blue O–Mediated Techniques for DNase Detection, J. Clin. Microbiology, vol. 21, No. 2, pp. 195–199 (1985).

Victor et al., Relationships Among Coagulase, Enterotoxin, and Heat–stable Deoxyribonuclease Production, by *Staphylococcus aureus* Applied Microb. vol. 18, No. 1, p. 126–127 (1969).

*Primary Examiner*—Carol A. Spiegel

[57] ABSTRACT

An article for detecting thermostable nuclease positive, potentially enterotoxigenic, staphylococci, containing unhydrolyzed nucleotides, toluidine blue O, and a binder, wherein the article is adapted for placement against a sample suspected of containing enterotoxigenic staphylococci. A method of detecting thermostable nuclease positive staphylococci in a sample utilizing the article, and a kit for the detection of thermostable nuclease positive staphylococci containing the article, are also described.

20 Claims, 2 Drawing Sheets

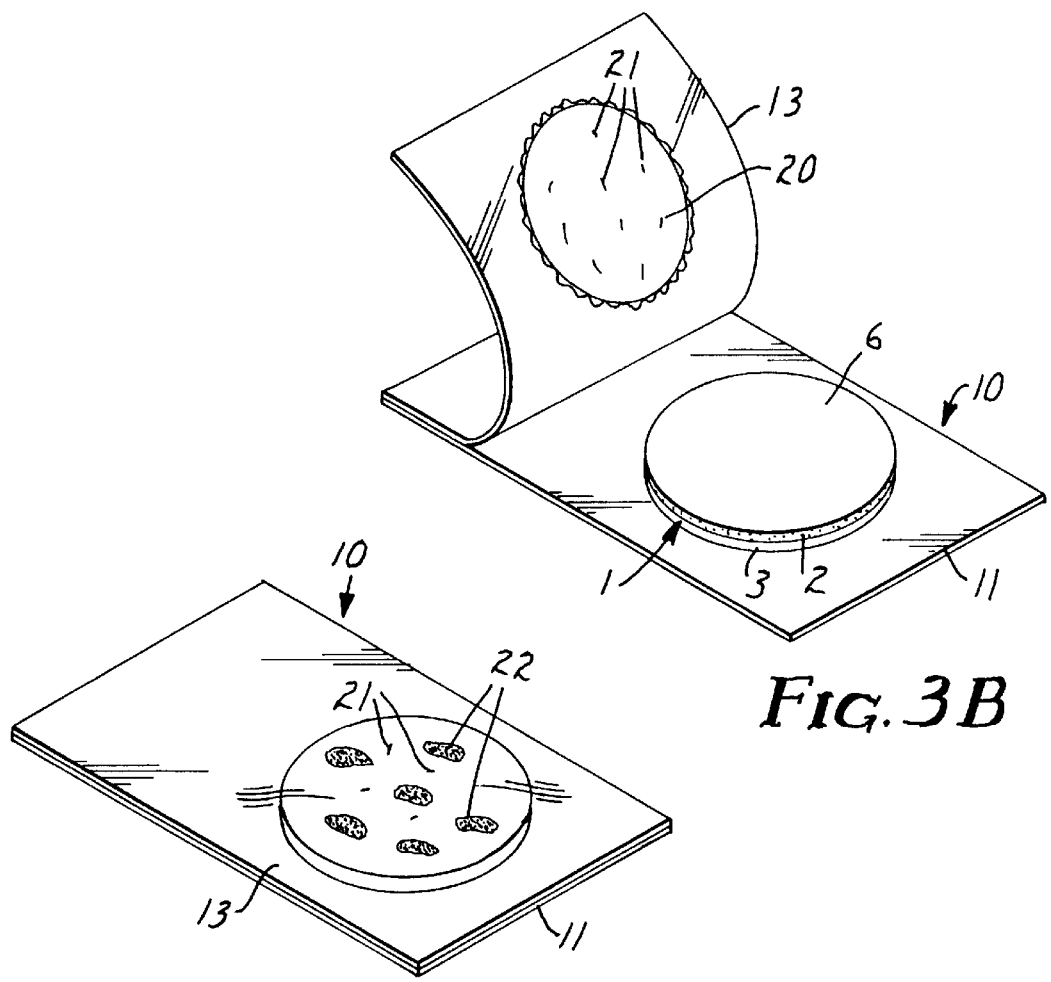

ARTICLE AND METHOD FOR DETECTION OF ENTEROTOXIGENIC STAPHYLOCOCCI

FIELD OF THE INVENTION

This invention relates to the detection of thermostable nuclease positive, potentially enterotoxigenic staphylococci, including Staphylococcus aureus, in samples, and to an article for such detection containing unhydrolyzed nucleotides, toluidine blue O, and a binder.

BACKGROUND OF THE INVENTION

Detection of potentially enterotoxigenic staphylococci is an important aspect of food processing, and may be used as a means of screening for indications of contamination during processing and for post-processing contamination. Food sample evaluations for potentially enterotoxigenic staphylococci can serve as a direct indication of the presence of potential pathogenic species in food. The detection of *Staphylococcus aureus* (*S. aureus*), a known enterotoxigenic species, is especially important in food processing. Other potentially enterotoxigenic species of Staphylococcus are also known, and the testing of samples for contamination with these species may also be important. In addition, the testing of patient samples to indicate possible pathogenic staphylococcal infection is of importance in the clinical setting.

Current methods for detecting *S. aureus* use Baird-Parker egg yolk-tellurite-pyruvate agar medium (abbreviated as BPA) for determining the presumptive presence of *S. aureus* in a fractional part of a sample. In this method, BPA plates are examined for the presence of "typical" colonies after 48 hours incubation. Samples of the colonies are then transferred to brain heart infusion for an additional incubation of up to 24 hours. The broth cultures are mixed with rabbit plasma for an additional 6 hours incubation. The culture-plasma mixtures are then evaluated for the presence of coagulation of the plasma (i.e., clotting). Cultures giving rise to a clot are considered to be "coagulase positive." A presumptive positive from BPA followed by a coagulase-positive result is considered to be confirmation of the presence of *S. aureus* in the sample.

The use of coagulase activity associated with the presence of *S. aureus* has also been thought to correlate with potential pathogenicity, including enterotoxin production. The tedious, time-consuming nature of the coagulase test, however, makes it impractical for routine testing of large numbers of samples.

The presence of *S. aureus* presently is confirmed in both the food processing and clinical settings by use of the coagulase test. For example, in the clinical setting, samples are reported as "CNS" (coagulase negative stash.) or "CPS" (coagulase positive staph.).

Two alternatives to the coagulase test have shown good statistical relation to the coagulase reaction of *S. aureus*: hyaluronidase and thermostable nuclease (TNase). The hyaluronidase system, however, is complex and costly. Testing for TNase activity was also tedious until Lachica et. al, Applied Microbiology 21(4), pp. 585–87 (1971), described the use of the metachromatic dye, toluidine blue O, dye for the detection of TNase by the differential staining in the presence of hydrolyzed and unhydrolyzed DNA.

The TNase detection method has been described and used in methods including (1) forming wells in a TBO/DNA agar-filled petri dish and placing boiled cultures within the well to determine the presence of TNase, (2) forming wells in a TBO/DNA agar medium cast on the surface of a microscope slide (or equivalent) and following the procedure of (1), (3) overlaying a Baird-Parker agar (or equivalent) plate with molten TBO/DNA agar after the developed BPA plate has been pre-incubated at 60° C. for at least 2 hours. (1), (2), and (3) give readable results in 2–4 hours from colonies or suspensions that are positive for TNase. Using these methods, various investigators have shown correlation of the TNase test with the coagulase test for *S. aureus* of up to 100%.

TNase activity has also been detected in other potentially enterotoxigenic Staphylococcus species, including some that are coagulase negative, e.g. *Staphylococcus hyicus*. TNase thus appears to be a better indicator of enterotoxigenicity than the coagulase test, i.e., most enterotoxigenic microorganisms are TNase-positive, while not all are coagulase-positive.

While current methods of TNase testing are reliable, their utility in testing or screening large numbers of samples is severely limited by the need to form wells or prepare molten agar in order to obtain results, which are time consuming and inefficient techniques in the context of testing large numbers of samples. It would thus be desirable to develop a TNase test for potentially enterotoxigenic staphylococci that would permit efficient and reliable testing or screening of large numbers of samples, in food processing or in clinical applications.

SUMMARY OF THE INVENTION

In one aspect, the invention features an article for detecting or confirming the presence of thermostable nuclease positive, potentially enterotoxigenic, staphylococci in a sample. The article contains unhydrolyzed nucleotides, toluidine blue O, and a binder. The article has at least two surfaces, and is adapted for placement against a sample suspected of containing enterotoxigenic staphylococci, such as *S. aureus*.

In preferred embodiments, the binder is guar gum. The article may further comprise lambda carrageenan as a contrast enhancing agent. The article may be of any thickness or shape. For example, the article may be disk-shaped, and as such, adapted for placement in a plate or well, or over a thin-film culture plate system, such as a Petrifilm ™. Preferably, the article has a thickness of between about 0.12–0.25 mm.

The article preferably contains a solid support, such as a polyester film, adjacent to one surface of the article. The article may further contain a protective material. The protective material may be adjacent to an exposed surface of the article. Where the article contains a solid support adjacent to one surface, the protective material may be adjacent to the opposite surface.

The article of the invention may contain reagents selected such that thermostable nuclease (TNase)-mediated hydrolysis of the unhydrolyzed nucleotides in the article will occur at a particular pH. Preferably, the article contains reagents selected such that nucleotide hydrolysis will occur at a pH of about 9.0. Alternatively, the article may preferably contain reagents such that nucleotide hydrolysis will occur at a pH of about 7.3.

In another aspect, the invention features a method of detecting thermostable nuclease positive staphylococci in a sample. The method includes the steps of (1) applying an article as described above for detecting thermostable nuclease positive staphylococci to a sample suspected of containing potentially enterotoxigenic staphylococci, and (2) confirming the presence or absence of thermostable nuclease positive staphylococci in the sample. The presence or absence is confirmed by detecting the presence or absence of a color change from blue to red or pink in the article.

In preferred embodiments, the sample is a food sample. In other preferred embodiments, the sample is a sample from a patient.

The culture medium to which the test sample is applied may be an agar-based medium, such as Baird-Parker Agar, or, more preferably, may be a thin-film culture plate device adapted to grow staphylococci.

The step of incubating the test sample in the culture medium preferably includes incubating the sample at about 37° C. for about 18–48 hours. The step of heating the sample preferably involves incubating the sample at at least about 60° C. for at least about 30 minutes.

The method may further comprise the step of quantitating the number of thermostable nuclease positive staphylococci in the sample. Quantitation may involve counting the number of colonies associated with a color change in the article, and correlating the number of colonies with a quantity of potentially enterotoxigenic staphylococci in the sample.

In another aspect, the invention features a kit for the detection of thermostable nuclease positive staphylococci in a sample. The kit contains reagents and nutrients for growing microorganisms from the sample, and an article for detecting thermostable nuclease positive staphylococci in a sample.

In preferred embodiments, the reagents and nutrients for growing microorganisms include a thin-film culture plate device adapted for growing staphylococci.

BRIEF DESCRIPTION OF THE FIGURES

FIGS. 3a–3c depict the use of one embodiment of the article of the invention with a thin-film culture plate device.

DETAILED DESCRIPTION OF THE INVENTION

Figure 1:
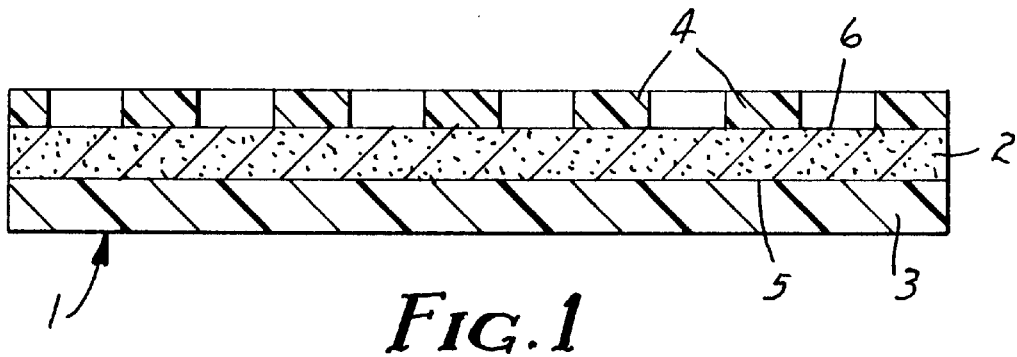
FIG. 1 is a cross-section view of a device showing one embodiment of the article of the invention.

This invention provides an article for detecting thermostable nuclease positive staphylococci in a sample. The article of the invention allows for rapid, efficient, and sensitive TNase analysis of large numbers of samples, and thus provides distinct advantages over currently used cumbersome and time-consuming TNase methods for detecting potentially enterotoxigenic, staphylococci, including *S. aureus*. The article also provides advantages over coagulase testing; TNase testing is more sensitive in the detection of potentially enterotoxigenic staphylococci because not all potentially enterotoxigenic staphylococci are coagulase positive, while most enterotoxigenic staphylococci are TNase positive. The article of the invention is especially useful in the analysis of food samples for the presence of *S. aureus*.

The article of the invention utilizes the principles that (1) the presence of thermostable nuclease (TNase) in a sample indicates the presence of possible enterotoxigenic staphylococci in the sample, and (2) the metachromatic dye toluidine blue O may be used to detect TNase activity in the presence of an acid polysaccharide and DNA.

Toluidine blue O is a metachromatic dye. Metachromasia is the property whereby a dye will not stain true because of complexes formed with some substances which result in an absorption spectrum different from that of the original dye. The true, or orthochromatic, staining of toluidine blue O is blue, whereas metachromatic staining results in a pink to red or violet color. When toluidine blue O is complexed with DNA it stains blue, but when complexed with an acid polysaccharide such as agarose, lambda carrageenan, heparin or the like, metachromasia occurs and the dye stains reddish pink to reddish violet.

Toluidine blue O has greater affinity for DNA than for an acid polysaccharide, and DNA stabilizes toluidine blue O in its orthochromic state of blue. When a DNAse-producing organism is present, however, the DNA is hydrolyzed, leaving the toluidine blue O unprotected from the acid polysaccharide and the dye changes to its reddish-pink to reddish-purple metachromatic form. A color change from blue to reddish-pink or reddish-purple is a positive identification of a DNase, e.g., a thermostable nuclease, producing microorganism.

Accordingly, the invention provides an article for detecting thermostable nuclease positive staphylococci. The article contains unhydrolyzed nucleotides, toluidine blue O, and a binder. The article is adapted for placement against a sample, usually a cultured sample, suspected of containing enterotoxigenic staphylococci.

The article is relatively dried, as opposed to liquid or molten, to an extent such that it may be stored in stable condition for use in testing. As such, the article is adapted for placement against a sample suspected of containing enterotoxigenic staphylococci. In use, the article of this invention is thus highly advantageous compared with currently available methods that require the formation of wells in freshly prepared agar, or the use of molten agar.

The unhydrolyzed nucleotides in the sample typically are in the form of DNA, which is readily available commercially (for example, salmon sperm DNA available from Difco Laboratories, Detroit, Mich.), but may be any nucleotide of sufficient size such that it stains blue with toluidine blue O, i.e., stabilizes toluidine blue O in its orthochromic state of blue. The term "unhydrolyzed nucleotides" as used herein thus refers to such nucleic acids. Toluidine blue O is available commercially (Sigma Chemical Company, St. Louis, Mo.).

The binder in the article may be any binder that causes metachromasia with respect to toluidine blue O, and that may be mixed with the other constituents of the article in solution and then coated and dried onto a substrate to form the article. Acid polysaccharides are known to cause metachromasia with respect to toluidine blue O, and are preferred binders. There are many binders that would be suitable for use in the article. Nonlimiting examples of suitable binders include agarose, guar gum, xanthan gum, locust bean gum, and other natural gums. A preferred binder is guar gum.

The article preferably may also include other constituents, such as calcium chloride (for TNase activity), sodium chloride (to provide appropriate ionic strength), or a buffer system (to control pH at which the TNase reaction occurs), such as Tris hydrochloride/Tris base.

The article of the invention may be prepared from solutions of varying pH. As such, the article contains reagents such that TNase-mediated nucleotide hydrolysis will occur at a selected pH. For example, as shown below in Example 1, an article in accordance with a preferred embodiment of the invention may be made from a pH 7.3 solution. Alternatively, as shown below in Example 2, an article in accordance with another preferred embodiment of the invention may be made from a pH 9.0 solution.

The optimal pH for TNase activity is 8.5–9.0. If the article is prepared such that the TNase reaction, between TNase in the sample and the unhydrolyzed nucleotides in the article, occurs at a pH in this optimal range, the color change in the article is readily detectable.

If the article is prepared such that the TNase reaction occurs at a pH outside (e.g., below) the optimal pH range for TNase activity, it may be advantageous to include a contrast enhancing agent in the article. For example, it is known that lambda carrageenan enhances the metachromatic shift and hence the contrast seen with toluidine blue O/DNA in the presence/absence of nucleic acids. See U.S. Pat. No. 4,241,181, the disclosure of which is incorporated herein by reference, by a description of the use of lambda carrageenan as a contrast enhancing agent. The inclusion of a contrast enhancing agent in the article is thus advantageous in systems where the TNase reaction may occur outside of the optimal pH range for thermonuclease activity.

Exemplary conditions for the preparation of articles in accordance with the invention are illustrated in the Examples that follow.

In general, the preparation of the article involves preparing a solution containing appropriate amounts of ingredients selected for inclusion in the article, including unhydrolyzed nucleotides, toluidine blue O, and a binder, cooling the solution and then coating the solution onto a solid support. The coated film is then dried to solidify the coated solution. To illustrate one preferred, but nonlimiting, embodiment, a solution containing 3.6 g/L salmon sperm DNA, 0.32 g/L toluidine blue O, and 1% (w/v) guar gum is coated onto a 0.18 mm polyester film solid support, and then dried 2–10 minutes at 200° F. The resultant dried coating may be of any desired thickness, but preferably has a thickness of about 0.12–0.25 mm. The ingredients, and the amounts thereof, may be selected such that the article is rigid or flexible, depending on what is desired for a particular application.

FIG. 1 shows the article in a preferred embodiment. A cross-section of a composite 1 is shown, which includes an article 2, a solid support 3, and a protective material 4. The article 2 contains the binder, unhydrolyzed nucleic acid, and toluidine blue O, as discussed above. As shown in FIG. 1, the article 2 has two surfaces 5 and 6. The solid support 3 is adjacent to a first surface 5, and the protective material 4 is adjacent to a second surface 6.

The solid support 3 may be a polymer film, such as a polyester film. The solid support 3 may be derived from molds for providing molded articles after drying, or the solid support 3 may be derived from a sheet material, allowing for the cutting, or punching, of articles of desired size or shape following coating and drying. The material used for the solid support 3 may be selected to impart any degree of rigidity or flexibility to the article/solid support composite. In addition, the article and/or article/solid support composite may be prepared in any shape or thickness, depending on what is desired for a particular application.

The solid support preferably is transparent or at least translucent, to allow the viewing of color changes that develop in the article in use. The solid support also provides stability to the article and protects it from damage.

The solid support may be selected such that it is peelable from the article, leaving the article free for use in testing without the solid support. For example, where a polyester film is used as the solid support, the solid support may be peelable from the article when the article becomes hydrated during use.

The article of the invention may further include a protective material. In FIG. 1, a protective material 4 is shown in cross-section. The protective material may be placed adjacent to an exposed surface of the article. For example, where a solid support is adjacent to one surface of the article, the protective material may be adjacent to the opposite surface. The protective material may be a polymer film or grid that protects the article in storage and transport, and may preferably operate as a spacer between articles, to separate the articles, which are hygroscopic after drying, from one another and permit stable storage and longer shelf-life. In FIG. 1, protective material 4 is shown as a grid in cross-section.

The protective material is selected such that it is peelable or removable from the surface of the article prior to use. Suitable materials for use as the protective material are known in the art.

As mentioned above, the article of the invention may be of any desired thickness, shape, or rigidity, and, if present, the solid support may be of any desired thickness and may be selected to impart any desired degree of rigidity or flexibility.

Figure 2:
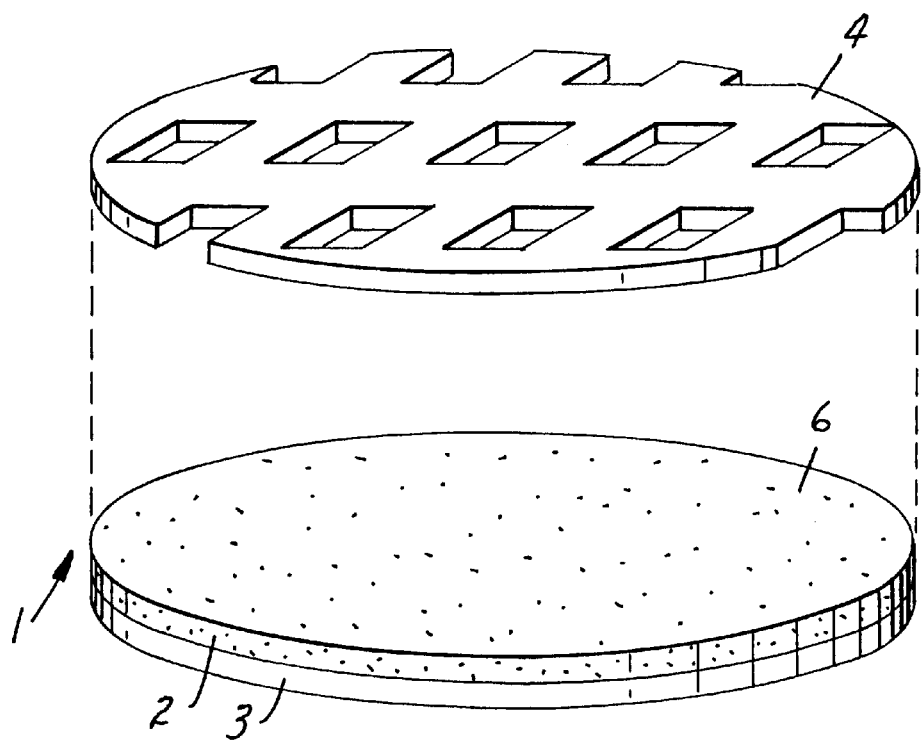
FIG. 2 is a partially exploded, perspective view of a device showing one embodiment of the article of the invention.

Referring now to FIG. 2, a composite 1 containing an article 2 of present invention is shown in partially exploded, perspective view. The article shown in FIG. 2 has a generally disk-like shape, but the article may have any shape desired for a particular application. The composite 1 depicted in FIG. 2 contains an article 2, a solid support 3, and, in exploded view, a protective material 4, shown as a grid. The article 2 has two surfaces, 5 and 6. The protective material 4, shown here as a grid in exploded view may be removed to reveal a surface 6 of the article for placement against a sample.

The article of the present invention is adapted for placement against a sample suspected of containing enterotoxigenic staphylococci, such as *Staphylococcus aureus*. As such, the article is capable of being pressed or applied onto the sample. The article is in a relatively dried form (as opposed to relatively liquid or molten form), permitting easy application to, or placement against, the sample. Upon application to the sample, the article becomes hydrated.

The sample is typically a cultured, heat-treated sample, for example, a sample cultured on a thin-layer culture plate device, such as a Petrifilm™ (available from 3 M, St. Paul, Minn.) or in an agar gel-based culture system such as Baird-Parker medium. Because thermonuclease enzyme does not diffuse far from a cultured enterotoxigenic staphylococcus colony, the sample to be tested should be prepared in a format which allows the article of the invention to be placed close to a presumptive enterotoxigenic staphylococcus colony. Because of thermostable nuclease diffusion limitations, a thin film culture plate format is especially preferred because a thin layer of culture medium in such a device advantageously permits placement of the article in very close proximity to the cultured sample containing presumptive enterotoxigenic staphylococcus colonies.

In use, the article is applied to or placed against, a sample such that the article contacts the sample. For example, where a sample suspected of containing enterotoxigenic staphylococci has been grown on an agar medium such as Baird-Parker agar, on a plate or in a well, and heat-treated (e.g., at 60° C. for 30 minutes) to inactivate non-thermostable nuclease activity, the article may be laid over the agar and thereby placed in contact with the sample. If TNase is present (correlative with the presence of enterotoxigenic staphylococci) the red or pink staining characteristic of toluidine blue O in the presence of hydrolyzed nucleic acids will develop within about one to four hours under proper conditions. The characteristic staining pattern is usually in the form of a red or pink "halo" surrounding the colony suspected of containing enterotoxigenic staphylococci.

In a thin film culture plate format, a test sample, e.g., a food sample that has been diluted and processed with a device such as a Stomacher, is applied to a film containing, for example, a gelling agent and nutrients for growing microorganisms. The nutrients may be selective for growing staphylococci. The test sample may also be a cultured sample from a patient, such as serum, skin or other sources, or the like, wherein the article is used to detect thermostable nuclease positive staphylococci in the patient sample.

The sample is then typically covered with a cover film and incubated at a temperature and for a time to allow microorganisms in the sample to multiply to detectable levels. If microorganisms are present in the sample, colonies of microorganisms will appear during incubation. Following incubation and heat treatment to inactivate non-thermostable nuclease activity, the article of the invention may then be placed in contact with the sample.

U.S. Pat. Nos. 4,565,783 and 5,232,838, the disclosures of which are incorporated by reference, describe in detail thin film culture plate devices suitable for use with the article of this invention.

FIGS. 3a–3c illustrate the use of the article of the invention with a thin film culture plate device. FIG. 3a shows an example of a thin film culture plate device 10 suitable for use with the article of the invention. The device contains a bottom film 11, to which a dried culture medium 12 is adhered. The culture medium may include, for example, medium adapted for growing staphylococci coated onto film as dried broth, or as powdered nutrients. A cover film 13 (shown peeled away from the bottom film 11) covers the culture medium 12 during storage and incubation. The cover film 13 preferably contains a gelling agent coated on a surface 14 that contacts the culture medium 12. Upon application of a test sample to the culture medium 12, the cover film 13 is applied over the bottom film 11 to contact the gelling agent with the sample and culture medium 13. The device is then incubated to allow microorganisms present in the sample to multiply and form colonies on the gelled culture medium. After incubation, the cultured sample is then preferably heated to a temperature sufficient to inactivate non-thermostable nuclease activity. The cover film 13 may then be peeled away from the bottom film 11, with the result, in this embodiment, that the gelled culture medium containing colonies is adhered to the surface 14 cover film.

FIG. 3a shows a peeled thin film culture plate device 10 following incubation. The gelled culture medium 20 containing colonies 21 is adhered to the cover film 13. Also shown in FIG. 3b is a composite 1 containing an article 2 of the present invention and a support layer 3, to be used in detecting thermostable nuclease. The composite 1 shown is disk-shaped, but may be of any shape appropriate for the setting in which it is used. In use, the composite 1 containing the article 2 is placed on the device such that an exposed surface 6 of the article 2 contacts the gelled culture medium 20 and colonies 21 when the cover film 13 is applied to the bottom film 11. For example, in the embodiment shown in FIG. 3b, the composite 1 is simply placed on the bottom film 11 with the exposed surface 6 of the article 2 facing upward toward the gelled, heat-treated culture medium. The cover film 13 is then applied, over the article 2, onto the bottom film 11, such that the composite 1 is disposed between the cover film 13 and bottom film 11. The device is then incubated, and viewed for color change to confirm the presence or absence of thermostable nuclease positive, potentially enterotoxigenic staphylococci.

FIG. 3c shows the thin film culture plate device 10 after incubation with an article 2 in accordance with the invention. The shaded areas 22, viewable through the transparent or at least translucent cover film 13, represent a color change which confirms the presence of thermostable nuclease positive staphylococci.

The article of the invention may be used in qualitative or quantitative testing for thermostable nuclease positive, potentially enterotoxigenic staphylococci. In qualitative testing, visualization of a blue to red or pink color change provides confirmation of the presence of thermostable nuclease positive staphylococci. In quantitative testing, use of the article allows for the number of TNase positive (potentially enterotoxigenic) staphylococcus colonies to be counted, and for the quantitation of such microorganisms using standard counting techniques.

Accordingly, the invention also provides a method of detecting thermostable nuclease positive, potentially enterotoxigenic, staphylococci in a sample. The method includes the steps of applying an article of the invention for detecting thermostable nuclease positive staphylococci to a sample suspected of containing enterotoxigenic staphylococci, and confirming the presence or absence of thermostable nuclease positive staphylococci in the sample.

Prior to the step of applying the article to the sample, the sample typically is prepared for testing by first applying a test sample suspected of containing enterotoxigenic staphylococci to a culture medium, incubating the test sample in the culture medium, and heating the sample at a temperature and for a time sufficient to inactivate non-thermostable nuclease activity. The incubation of the test sample is typically performed at 30–37° C. for about 18–48 hours, and the heating of the sample to inactivate non-thermostable nuclease activity is performed at at least about 60° C. for about 30 minutes.

The sample to which the article is applied in the method of the invention may be an agar-based culture, such as a Baird-Parker agar culture, or a thin film culture plate device as described herein. The method may further include the step of quantitating enterotoxigenic or potentially enterotoxigenic staphylococci in the sample. The step of quantitating may involve counting the number of colonies associated with color change in the article, and correlating that number with a quantity of enterotoxigenic staphylococci in the sample, using techniques known in the art.

The invention further provides a kit for the detection of thermostable nuclease positive, potentially enterotoxigenic, staphylococci. The kit may be adapted for any of the wide variety of formats for growing microorganisms, e.g., agar, thin film culture plate, and the like. The kit of the invention includes reagents and nutrients for growing microorganisms, preferably in the form of a thin film culture plate device, and further includes an article according to this invention for detecting thermostable nuclease positive staphylococci.

The invention may be illustrated by way of the following examples.

EXAMPLE I

Preparation of pH 7.3 Articles

The following ingredients used in preparation of articles for detection of *Staphylococcus aureus:*
DNA (Difco Laboratories, Detroit, Mich.) 3.6 g/L
Toluidine blue O (Sigma Chemical Company, 0.32 g/L St. Louis, Mo.)
Calcium chloride, anhydrous (Sigma, St. 1.1 mg/L Louis, Mo.)
Sodium chloride (Sigma, St. Louis, Mo.) 10 g/L
Tris hydrochloride (Sigma, St. Louis, Mo.) 6.85 g/L
Tris base (Sigma, St. Louis, Mo.) 0.8 g/L
lambda carrageenan (Sigma, St. Louis, Mo.) 0.4 g/L
Guar gum (Rhone-Poulenc Food Ingredients, 10 g/L Cranbury, N.J.) pH 7.3

The medium (designated pH 7.3) was prepared as follows: all reagents (less the TBO and guar gum) were mixed together in 1 liter of deionized water. The suspension was mixed with constant stirring and heated to boiling. The TBO was added to the mixture and removed from the heat while maintaining the stirring. The suspension was then mixed with an air mixer (with vigorous vortex) and the guar gum was added and mixed until uniform. Suspension was cooled overnight at 4° C. and then coated with a knife coater onto 0.18 mm polyester film. Knife gaps of 0.12–0.25 mm were evaluated (coating weights of 0.05–0.10 g/24 square inches). Films were heat dried for 2–10 minutes at 200° F.

EXAMPLE II

Preparation of pH 9.0 Articles

Another medium was made from the following components:
DNA (Difco) 3.6 g/L
Toluidine blue O (Sigma) 0.32 g/L
Calcium chloride, anhydrous (Sigma) 1.1 mg/L
Sodium chloride (Sigma) 10 g/L
Tris hydrochloride (Sigma) 0.76 g/L
Tris base (Sigma) 5.47 g/L
Guar gum (Rhone-Poulenc) 10 g/L pH 9.0

This medium (designated pH 9) was prepared identical to the pH 7.3 medium and coated similarly. Coating weight ranges were the same for both media. Coated films were cut into 2-inch squares for evaluation.

EXAMPLE III

Preparation of TBO/DNA Agar

These media were compared with TBO/DNA agar made as follows:
DNA (Difco) 0.3 g/L
Toluidine blue O (Sigma) 0.082 g/L
Calcium chloride, anhydrous (Sigma) 1.1 mg/L
Sodium chloride (Sigma) 10 g/L
Tris hydrochloride (Sigma) 0.76 g/L
Tris base (Sigma) 5.47 g/L
Agar (Difco) 10 g/L pH 9.0

The medium (designated: TBO/DNA agar) was prepared as follows: all reagents (less the TBO) were mixed together in 1 liter of deionized water. The suspension was mixed with constant stirring and heated to boiling. The TBO was added to the mixture and the suspension was removed from the heat while maintaining the stirring. The mixture was autoclaved (250° F./15 atm/15 minutes). Medium was tempered to 46° C. and then dispensed into 15×100 mm petri dishes (12–15 milliliters/plate). After solidifying, plates were inverted and incubated at room temperature, overnight. Plates were then maintained at 4° C. until used.

EXAMPLE IV

Detection of *Staphylococcus aureus*

Overnight (37° C.) trypticase soy broth (DiMed, St. Paul, Minn.) cultures of the following staphylococci isolates were prepared:

| American Type Culture Collection #; coagulase result | | | |
|---|---|---|---|
| S. aureus | S. species | S. epidermidis | S. simulans |
| 27600 + | 23235 + | 35547 – | 11631 – |
| 13301 + | 13566 + | 14990 – | |
| 13565 + | 13567 + | 155 – | |
| 12600 + | | | |
| 27659 + | | | |
| 832 + | | | |
| 12598 + | | | |
| 25923 + | | | |
| 27661 + | | | |
| S. saprophyticus | S. intermedius | Enterococcus fecaelis | |
| 3552 – | 29663 – | 29212 – | |

Cultures were diluted into Butterfield's Phosphate buffer to approximately 50 cfu/mm. 1 milliliter samples of each diluted culture were plated onto 3 identical 3M™ Petrifilm™ Aerobic Count plates and incubated at 37° C. for 18–24 hours. Films were preincubated at 60° C. for 1 hour. Two plates were set aside to evaluate the pH 9 and pH 7.3 confirmatory disks.

The Petrifilm™ plates for agar evaluation were separated such that the film with the attached gel was separated from the other film. These films (with gel) were overlaid onto the surface of the agar plates and then incubated at 37° C. for the evaluation.

The confirmatory disks were evaluated by separating the Petrifilm™ plate films and then placing the disks (coated side) in contact with the gel. Petrifilm™ plate films were then re-sealed and then incubated at 37° C., as were the agar plates. Results were as follows:

| Isolate | Coagulase | TBO/DNA agar | pH 9.0 | pH 7.3 |
|---|---|---|---|---|
| 27600 | + | + | + | + |
| 13301 | + | + | + | + |
| 13565 | + | + | + | + |
| 12600 | + | + | + | + |
| 27659 | + | + | + | + |
| 832 | + | + | + | + |
| 12598 | + | + | + | + |
| 25923 | + | + | + | + |
| 27661 | + | + | + | + |
| 23235 | + | + | + | + |
| 13566 | + | + | + | + |
| 13567 | + | + | + | + |
| 35547 | – | – | – | – |
| 14990 | – | – | – | – |
| 155 | – | – | – | – |
| 11631 | – | – | – | – |
| 35552 | – | – | – | – |
| 29663 | – | – | – | – |
| 29212 | – | – | – | – |

Plates were read every 30 minutes. All colonies were positive within 90 minutes of the 37° C. incubation. No differences were noted between the disk results (pH 9 or pH 7.3) or the agar plate results.

EXAMPLE V

Detection of *Staphylococcus Aureus* on Baird Parker Agar

In this example, overnight broth cultures were diluted into Butterfield's Phosphate buffer to approximately 500 cfu/milliliter. 0.1 milliliters of the diluted cultures were plated onto Baird-Parker agar (DiMed) and then incubated at 37° C. for 48 hours. After 48 hours, the plates were incubated at 60° C. for 2 hours. TBO/DNA agar was prepared as outlined above except that after tempering to 46° C., 12–15 milliliters were dispensed over the BPA plate lawns. The pH 9.0 and pH 7.3 disks were placed over the surface of the agar plates so that the coated side came in contact with the agar. Plates were then incubated at 37° C. and then read every 30 minutes, with the following results:

| Isolate | Coagulase | TBO/DNA agar | pH 9.0 | pH 7.3 |
| --- | --- | --- | --- | --- |
| 27600 | + | + | + | + |
| 13301 | + | + | + | + |
| 13565 | + | + | + | + |
| 12600 | + | + | + | + |
| 27659 | + | + | + | + |
| 832 | + | + | + | + |
| 12598 | + | + | + | + |
| 25923 | + | + | + | + |
| 27661 | + | + | + | + |
| 23235 | + | + | + | + |
| 13566 | + | + | + | + |
| 13567 | + | + | + | + |
| 35547 | − | − | − | − |
| 14990 | − | − | − | − |
| 155 | − | − | − | − |
| 11631 | − | − | − | − |
| 35552 | − | − | − | − |
| 29663 | − | − | − | − |
| 29212 | − | − | − | − |

All colonies on the plates were positive within 2 hours of the 37° C. incubation. No difference was noted between the disks and the TBO/DNA agar.

EXAMPLE VI

Detection of *Staphylococcus aureus* Using Petrifil™ Format

The pH 7.3 confirmatory disks were evaluated as a confirmation in a Petrifilm™ format using the following growth medium:

| | |
| --- | --- |
| Tryptone (Difco) | 20 g/L |
| Mannitol (Sigma) | 10 g/L |
| Lithium Chloride (Sigma) | 10 g/L |
| Guar gum (Rhone-Poulenc) | 10 g/L |
| Phenol Red (Sigma) | 0.4 g/L |
| | pH 7.5 |

The medium (designated PSA) was prepared as follows: all reagents were mixed together in 1 liter of deionized water. The suspension was mixed with constant stirring with an air mixer (with vigorous vortex) and heated to 80° C. Suspension was cooled overnight at 4° C. and then coated with a knife coater onto 0.18 mm polyester film. Knife gaps of approximately 31 mm were evaluated (coating weights of 0.22–0.25 g/24 square inches). Films were heat dried for 2–10 minutes at 200° F.

0.05 cm polystyrene foam was laminated onto the PSA coated film using an acrylic acid based adhesive. A 5 cm diameter circle was removed from the approximate center of each polystyrene plate to provide for a well. On top of the foam (covering the entire surface) was attached (by a piece of hinge tape) a piece of polypropylene film (0.1 mm). On one side of this film was coated an acrylic acid adhesive containing 0.15 g/L triphenyl tetrazolium chloride. Guar gum was powder coated onto this adhesive at approximately 0.4 g/24 square inches.

Overnight (37° C.) trypticase soy broth (DiMed, St. Paul, Minn.) cultures of the following staphylococci isolates were prepared:

| American Type Culture Collection #; coagulase result | | | |
| --- | --- | --- | --- |
| S. aureus | S. species | S. epidermidis | S. simulans |
| 27600 + | 23235 + | 35547 − | 11631 − |
| 13301 + | 13566 + | 14990 − | |
| 13565 + | 13567 + | 155 − | |
| 12600 + | | | |
| 27659 + | | | |
| 832 + | | | |
| 12598 + | | | |
| 25923 + | | | |
| 27661 + | | | |
| S. saprophyticus | S. intermedius | Enterococcus fecaelis | |
| 35552 − | 29663 − | 29212 − | |

Cultures were diluted into Butterfield's Phosphate buffer to approximately 50 cfu/milliliter. 1 milliliter samples of each diluted culture were plated onto each of two PSA plates and incubated at 37° C. for 24 hours. Films were then preincubated at 60° C. for 1 hour. Two plates were set aside to evaluate pH 7.3 coated solution (disks) and the TBO/DNA agar.

The Petrifilm™ plates for agar evaluation were separated such that the film with the attached gel was separated from the other film. These films (with gel) were overlaid onto the surface of the agar plates and then incubated at 37° C. for the evaluation.

The pH 7.3 confirmatory disks were evaluated by separating the Petrifilm™ plate films and then placing the disks (coated side) in contact with the gel. Petrifilm™ plate films were then re-sealed and then incubated at 37° C. as were the agar plates. Results were as follows:

| Isolate | Coagulase | TBO/DNA agar | pH 7.3 |
| --- | --- | --- | --- |
| 27600 | + | + | + |
| 13301 | + | + | + |
| 13565 | + | + | + |
| 12600 | + | + | + |
| 27659 | + | + | + |
| 832 | + | + | + |
| 12598 | + | + | + |
| 25923 | + | + | + |
| 27661 | + | + | + |
| 23235 | + | + | + |
| 13566 | + | + | + |
| 13567 | + | + | + |
| 35547 | − | − | − |
| 14990 | − | − | − |
| 155 | − | − | − |

-continued

| Isolate | Coagulase | TBO/DNA agar | pH 7.3 |
|---------|-----------|--------------|--------|
| 11631   | −         | −            | −      |
| 35552   | −         | −            | −      |
| 29663   | −         | −            | −      |
| 29212   | −         | −            | −      |

Plates were read every 30 minutes. All colonies were positive within 90 minutes of the 37° C. incubation. No differences were noted between the disk result (pH 7.3) or the agar plate result.

Other embodiments are within the scope of the claimed invention.

What is claimed is:

1. A dry article for determining the presence or amount of thermostable nuclease positive staphylococci in a sample suspected of containing said thermostable nuclease positive staphylococci, said dry article comprising unhydrolyzed nucleotides, toluidine blue O, and a binder, said article further comprising at least two surfaces wherein at least one of said surfaces of said article is adapted for placement against said sample.

2. The article of claim 1 wherein said binder is guar gum.

3. The article of claim 1 wherein said article further comprises lambda carrageenan.

4. The article of claim 1 wherein a solid support is provided adjacent to one surface of said article.

5. The article of claim 4 wherein said solid support is a polyester film.

6. The article of claim 4 wherein a protective cover is provided adjacent said surface adapted for placement against said sample.

7. The article of claim 1 wherein said article has a thickness of about 0.12 mm to about 0.25 mm.

8. The article of claim 1 wherein said article comprises reagents to effect thermostable nuclease-mediated hydrolysis of said nucleotides at a pH of about 7.3.

9. The article of claim 1 wherein said article comprises reagents to effect thermostable nuclease-mediated hydrolysis of said nucleotides at a pH of about 9.0.

10. A method of determining the presence or amount of thermostable nuclease positive staphylococci in a cultured sample containing bacterial colonies, comprising the steps of:

contacting a dry article for determining the presence or amount of said thermostable nuclease positive staphylococci with said sample, wherein said dry article comprises unhydrolyzed nucleotides, toluidine blue O, and a binder, further comprises at least two surfaces wherein at least one of said surfaces is adapted for placement against said sample, and wherein said sample comprises nutrient medium selective for growing staphylococci and has been heat-treated to inactivate non-thermostable nuclease activity; and determining the presence or amount of said thermostable nuclease positive staphylococci in said sample by detecting the presence or amount of a color change from blue to red or pink in said article.

11. The method of claim 10 wherein said sample is a food sample.

12. The method of claim 10 wherein said sample is a sample from a patient.

13. The method of claim 10 wherein said sample is a sample cultured in a film culture plate device adapted to grow staphylococci.

14. The method of claim 10 wherein said heat-treatment comprises incubating said sample at at least about 60° C. for about 30 minutes.

15. The method of claim 10 wherein said cultured sample is a gelled sample cultured on a plate or in a well.

16. The method of claim 15 wherein said gel plate or well-based cultured sample comprises Baird-Parker medium.

17. The method of claim 10 wherein the amount of said thermostable nuclease positive staphylococci in said sample is determined.

18. The method of claim 17, wherein said amount is determined by counting a number of said colonies in said sample exhibiting said color change in said article, and correlating said number with said amount of said thermostable nuclease positive staphylococci in said sample.

19. A kit for determining the presence or amount of thermostable nuclease positive staphylococci in a sample, comprising reagents and nutrients selective for growing staphylococci from said sample, and a dry article for determining the presence or amount of thermostable nuclease positive staphylococci in said sample, wherein said dry article has at least two surfaces and comprises unhydrolyzed nucleotides, toluidine blue O, and a binder, and wherein at least one surface of said article is adapted for placement against said sample.

20. The kit of claim 19 wherein said reagents and nutrients comprise a film culture plate device adapted to grow staphylococci.

* * * * *